(12) United States Patent
Roh et al.

(10) Patent No.: US 11,358,904 B2
(45) Date of Patent: Jun. 14, 2022

(54) DIELECTRIC MATERIAL, METHOD OF MANUFACTURING THEREOF, AND DIELECTRIC DEVICES AND ELECTRONIC DEVICES INCLUDING THE SAME

(71) Applicant: SAMSUNG ELECTRONICS CO., LTD., Suwon-si (KR)

(72) Inventors: Jong Wook Roh, Anyang-si (KR); Daejin Yang, Yeongju-si (KR); Doh Won Jung, Seoul (KR); Chan Kwak, Yongin-si (KR); Hyungjun Kim, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 1052 days.

(21) Appl. No.: 15/908,193

(22) Filed: Feb. 28, 2018

(65) Prior Publication Data
US 2018/0257991 A1   Sep. 13, 2018

(30) Foreign Application Priority Data
Mar. 10, 2017  (KR) .................. 10-2017-0030660

(51) Int. Cl.
*C04B 35/491* (2006.01)
*C04B 35/468* (2006.01)
(Continued)

(52) U.S. Cl.
CPC ............ *C04B 35/491* (2013.01); *C01G 29/00* (2013.01); *C01G 29/006* (2013.01); *C01G 35/00* (2013.01);
(Continued)

(58) Field of Classification Search
CPC ..... C04B 35/491; C04B 35/47; C04B 35/472; C04B 35/4682; C04B 2235/85;
(Continued)

(56) References Cited

U.S. PATENT DOCUMENTS 4,309,295 A    1/1982  McSweeney
4,362,637 A   12/1982  Matsuo et al.
(Continued)

FOREIGN PATENT DOCUMENTS

CN         1527331 A     9/2004
CN       105431955 A     3/2016
(Continued)

OTHER PUBLICATIONS

Fukunaga, Masanori, Masaki Takesada, and Akira Onodera. "Ferroelectricity in layered perovskites as a model of ultra-thin films." World Journal of Condensed Matter Physics 6.3 (2016): 224-243. (Year: 2016).*

(Continued)

*Primary Examiner* — Karl E Group
*Assistant Examiner* — Cameron K Miller
(74) *Attorney, Agent, or Firm* — Cantor Colburn LLP

(57) ABSTRACT

A dielectric material, a method of manufacturing thereof, and a dielectric device and an electronic device including the same. A dielectric material includes a layered metal oxide including a first layer having a positive charge and a second layer having a negative charge which are laminated, a monolayer nanosheet exfoliated from the layered metal oxide, a nanosheet laminate of the monolayer nanosheets, or a combination thereof, wherein the dielectric material includes a two-dimensional layered material having a two-dimensional crystal structure and the two-dimensional layered material is represented by Chemical Formula 1.

20 Claims, 12 Drawing Sheets

(51) Int. Cl.

| | |
|---|---|
| C04B 35/47 | (2006.01) |
| C04B 35/472 | (2006.01) |
| H01G 4/10 | (2006.01) |
| C01G 41/00 | (2006.01) |
| C01G 41/02 | (2006.01) |
| C01G 29/00 | (2006.01) |
| C01G 35/00 | (2006.01) |
| C07C 211/63 | (2006.01) |
| C07C 211/01 | (2006.01) |
| H01C 7/115 | (2006.01) |
| C04B 35/475 | (2006.01) |
| H01G 4/12 | (2006.01) |
| C04B 35/495 | (2006.01) |
| H01C 7/00 | (2006.01) |

(52) U.S. Cl.
CPC ......... *C01G 35/006* (2013.01); *C01G 41/006* (2013.01); *C01G 41/02* (2013.01); *C04B 35/4682* (2013.01); *C04B 35/47* (2013.01); *C04B 35/472* (2013.01); *C04B 35/475* (2013.01); *C04B 35/495* (2013.01); *C07C 211/01* (2013.01); *C07C 211/63* (2013.01); *H01C 7/115* (2013.01); *H01G 4/10* (2013.01); *H01G 4/1227* (2013.01); *C01P 2002/22* (2013.01); *C01P 2004/03* (2013.01); *C01P 2004/24* (2013.01); *C01P 2006/40* (2013.01); *C04B 2235/3251* (2013.01); *C04B 2235/3258* (2013.01); *C04B 2235/3298* (2013.01); *C04B 2235/5292* (2013.01); *C04B 2235/5436* (2013.01); *C04B 2235/5445* (2013.01); *C04B 2235/85* (2013.01); *H01C 7/008* (2013.01)

(58) Field of Classification Search
CPC ........ H01G 4/10; C01G 41/006; C01G 41/02; C01G 29/006; C01G 35/006; C07C 211/63; C07C 211/01; C01P 2006/40; C01P 2002/22; H01C 7/008
See application file for complete search history.

(56) References Cited

U.S. PATENT DOCUMENTS

| | | | |
|---|---|---|---|
| 4,403,236 | A | 9/1983 | Mandai et al. |
| 5,509,558 | A | 4/1996 | Imai et al. |
| 5,638,252 | A | 6/1997 | Drab et al. |
| 5,753,934 | A | 5/1998 | Yano et al. |
| 5,757,610 | A | 5/1998 | Wada et al. |
| 5,801,105 | A | 9/1998 | Yano et al. |
| 5,804,823 | A | 9/1998 | Ramer et al. |
| 6,143,679 | A | 11/2000 | Nagasawa et al. |
| 6,207,082 | B1 | 3/2001 | Suzuki et al. |
| 6,292,355 | B1 | 9/2001 | Kang et al. |
| 6,795,296 | B1 | 9/2004 | Palanduz et al. |
| 6,900,977 | B2 | 5/2005 | Nakamura et al. |
| 7,911,927 | B2 | 3/2011 | Koinuma et al. |
| 8,184,426 | B2 | 5/2012 | Osada et al. |
| 8,885,322 | B2 | 11/2014 | Chai |
| 9,187,842 | B2 | 11/2015 | Nakajima et al. |
| 9,543,500 | B2 | 1/2017 | Osada et al. |
| 9,656,878 | B2 | 5/2017 | Yashima et al. |
| 9,742,005 | B2 | 8/2017 | Choi et al. |
| 2010/0226067 | A1 | 9/2010 | Osada et al. |
| 2011/0147060 | A1 | 6/2011 | Osada et al. |
| 2012/0217615 | A1 | 8/2012 | Tatekawa |
| 2012/0270720 | A1* | 10/2012 | Tanabe .................. C03C 14/004 501/138 |
| 2013/0065065 | A1* | 3/2013 | Nakajima ............... C03C 17/23 428/432 |
| 2013/0234293 | A1 | 9/2013 | Kawamoto |
| 2013/0286541 | A1 | 10/2013 | Kawamoto |
| 2016/0141111 | A1 | 5/2016 | Sato et al. |

FOREIGN PATENT DOCUMENTS

| | | |
|---|---|---|
| EP | 0634756 A2 | 1/1995 |
| JP | 1997110592 A | 4/1997 |
| JP | 2011184274 A | 9/2011 |
| JP | 2014144904 A | 8/2014 |
| JP | 2014152052 A | 8/2014 |
| JP | 2015046582 A | 3/2015 |
| JP | 2015119184 A | 6/2015 |
| KR | 940011059 B1 | 11/1994 |
| KR | 1020120091655 A | 8/2012 |
| KR | 1020140049190 A | 4/2014 |
| KR | 1398553 B1 | 5/2014 |
| KR | 101405078 B1 | 6/2014 |
| KR | 1020150024761 A | 3/2015 |
| KR | 101522666 B1 | 5/2015 |
| KR | 1020150061014 A | 6/2015 |
| KR | 1020160080866 A | 7/2016 |
| WO | 2015056558 A1 | 4/2015 |

OTHER PUBLICATIONS

Funakubo, Hiroshi. "Degradation-free dielectric property using bismuth layer-structured dielectrics having natural superlattice structure." Journal of the Ceramic Society of Japan 116.1360 (2008): 1249-1254. (Year: 2008).*

Office Action dated May 17, 2021 of the corresponding Korean Patent Application No. 10-2017-0042201.

Masanori Fukunaga, et al., "Ferroelectricity in Layered Perovskites as a Model of Ultra-Thin Films", World Journal of Condensed Matter Physics, 2016, 6, 224-243.

Korean Office Action for Korean Patent Application No. 10-2017-0030659 dated Jan. 20, 2021.

Office Action for Chinese Patent Application No. 201810269346.X dated Mar. 30, 2021.

Extended European Search Report dated Aug. 1, 2018, of the corresponding European Patent Application No. 18164562.3.

Extended European Search Report dated Jun. 22, 2018, of the corresponding European Patent Application No. 18152527.0.

Li et al., "Solution-Based Fabrication of Perovskite Nanosheet Films and Their Dielectric Properties", Japanese Journal of Applied Physics, 48, 2009, pp. 1-5.

Liu et al., "A New n=4 Layered Ruddlesden-Popper Phase K2.5Bi2.5Ti4O13 Showing Stoichiometric Hydration", Inorganic Chemistry, 55, 2016, pp. 1403-1411.

Maeda K et al., "Perovskite oxide nanosheets with tunable band-edge potentials and high photocatalytic hydrogen-evolution activity", Angewandte Chemie, Sep. 26, 2014, p. 13164-13168, vol. 53.

Minoru Osada et al., "A- and B-Site Modified Perovskite Nanosheets and Their Integrations into High-k Dielectric Thin Films", Applied Ceramic Technology, Dec. 5, 2011, pp. 29-36, vol. 9, Issue 1.

Minoru Osada, et al., "Two-Dimensional Dielectric Nanosheets: Novel Nanoelectronics from Nanocrystal Building Blocks", Adv. mater. 2012, 24, 210-228.

Schaak et al., "Perovskites by Design: A Toolbox of Solid-State Reactions", Chem. Mater. vol. 14, 2002. 1455-1471.

Schaak et al., "Prying Apart Ruddlesden-Popper Phases: Exfoliation into Sheets and Nanotubes for Assembly of Perovskite Thin Films", Chem. Mater. vol. 12, 2000, pp. 3427-3434.

Notice of Allowance dated Oct. 27, 2021, of Korean Patent Application No. KR 10-2017-0042201.

Christian Ziegler et al., "Two-Dimensional Transition Metal Oxide Nanosheets for Nanoarchitectonics," 2015,. Dissertation, LMU Munchen: Faculty of Chemistry and Pharmacy; maximilians university, pp. 1-230.

Office Action dated Aug. 24, 2021 of the corresponding KR Patent Application No. 10-2017-0030660.

Woong-Hee Lee et al., "Synthesis of Sr2Nb3O10 nanosheets and their application for growth of thin film using an alectrophoretic method," J Am Ceram Soc., 2017, pp. 1098-1107, vol. 100.

(56) References Cited

OTHER PUBLICATIONS

Notice of Allowance dated Mar. 23, 2022 of the corresponding Korean Patent Application No. 10-2017-0030660.

* cited by examiner

DIELECTRIC MATERIAL, METHOD OF MANUFACTURING THEREOF, AND DIELECTRIC DEVICES AND ELECTRONIC DEVICES INCLUDING THE SAME

CROSS-REFERENCE TO RELATED APPLICATION

This application claims priority to and the benefit of Korean Patent Application No. 10-2017-0030660 filed in the Korean Intellectual Property Office on Mar. 10, 2017, and all the benefits accruing therefrom under 35 U.S.C. § 119, the entire contents of which are incorporated herein by reference.

BACKGROUND

1. Field

A dielectric material, a method of manufacturing thereof, and a dielectric device and an electronic device including the same are disclosed.

2. Description of the Related Art

A multi-layer ceramic condenser (MLCC), which is a small-size condenser having a large capacity, is an electronic device obtained by alternately laminating a dielectric ceramic composition and an internal electrode and firing the same simultaneously. According to the ongoing requirements for electronic devices to provide a small size, a thin film, and a greater capacity, there remains an increasing need to develop a condenser having further smaller size and greater thinness, and greater capacity than the conventional multi-layered ceramic condenser structure.

In addition, an intergranular insulation type capacitor of dielectric materials exhibiting good dielectric characteristics may form an intergranular insulation layer between crystal grains having conductivity or semi-conductivity, e.g., conductive or semiconductive crystal grains, so the intergranular insulation type capacitor may have a greater apparent dielectric constant than the conventional multi-layered ceramic condenser including an entirety of the relatively thick ceramic layer as a dielectric layer, and down-sizing and greater capacity may be possible.

An apparent dielectric constant of the intergranular insulation type capacitor tends to be generally proportional to a particle size and inversely proportional to a thickness of the intergranular insulation layer. However, a dielectric constant of the intergranular insulation layer is also decreased with a decreased thickness of the intergranular insulation layer, and the intergranular insulation layer may have problems in that the thickness of the intergranular insulation layer may be maintained in a predetermined range taking into account or considering the dielectric constant of the intergranular insulation type capacitor.

SUMMARY

An embodiment provides a dielectric material having a large dielectric constant even in a region having a thickness of several nanometers to several tens of nanometers and a method of manufacturing thereof.

An embodiment provides a dielectric device having improved capacity characteristics as well as realizing possible down-sizing and including a thin film by including the dielectric material and an electronic device including the same.

According to an embodiment, a dielectric material includes a layered metal oxide including a first layer having a positive charge and a second layer having a negative charge which are laminated, a monolayer nanosheet exfoliated from the layered metal oxide, a nanosheet laminate of the monolayer nanosheets, or a combination thereof, wherein the dielectric material includes a two-dimensional layered material having a two-dimensional crystal structure and the two-dimensional layered material is represented by Chemical Formula 1

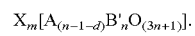  Chemical Formula 1

$$X_m[A_{(n-1-d)}B'_nO_{(3n+1)}].$$

In Chemical Formula 1, X includes H, $Bi_2O_2$, a cationic compound, or a combination thereof, A includes Bi, Ba, Ca, Pb, Sr, or a combination thereof, B' includes W, Mo, Cr, Ta, Nb, Ti, or a combination thereof, $1 \leq m \leq 2$, $n \geq 1$, $0 \leq d \leq 1$, and $n-1-d \geq 0$.

The monolayer nanosheet may include a second layer exfoliated from the layered metal oxide.

The monolayer nanosheet may include the cationic compound attached to a surface of the second layer.

The two-dimensional layered material may have the average longitudinal diameter of about 0.1 micrometers (μm) to about 100 μm.

The two-dimensional layered material may have an average thickness of less than or equal to about 100 nanometers (nm).

X may include the cationic compound, and the cationic compound may include a (C1 to C16 alkyl)ammonium compound, a (C1 to C16 alkyl)amine compound, or a combination thereof.

The cationic compound may include a tetramethylammonium compound, a tetraethylammonium compound, a tetrapropylammonium compound, a tetrabutylammonium compound, a methylamine compound, an ethylamine compound, a propylamine compound, a butylamine compound, an amine polymer, or a combination thereof.

The dielectric material may have a dielectric constant of greater than or equal to about 70 at a relative density of about 50% to about 90%.

A method of manufacturing a dielectric material according to an embodiment includes preparing a layered metal oxide including a first layer having a positive charge and a second layer having a negative charge which are laminated, acid-treating the layered metal oxide to exchange the first layer with protons, colloidizing the acid-treated layered metal oxide to replace the protons by a cationic compound, and exfoliating the monolayer nanosheet including the second layer from the colloidized layered metal oxide.

The cationic compound may include a tetramethylammonium compound, a tetraethylammonium compound, a tetrapropylammonium compound, a tetrabutylammonium compound, a methylamine compound, an ethylamine compound, a propylamine compound, a butylamine compound, an amine polymer, or a combination thereof.

The monolayer nanosheet may include the cationic compound attached to a surface of the second layer.

According to an embodiment, a dielectric device includes a plurality of crystal grains including a semi-conductive or conductive material, and a grain boundary insulation layer between the crystal grains wherein the grain boundary insulation layer covers at least one portion of a surface of at least one of the crystal grain and a dielectric material including a two-dimensional layered material represented by Chemical Formula 1 and having a two-dimensional crystal structure.

$$X_m[A_{(n-1-d)}B'_nO_{(3n+1)}]$$  Chemical Formula 1

In Chemical Formula 1, X includes H, $Bi_2O_2$, a cationic compound, or a combination thereof, A includes Bi, Ba, Ca, Pb, Sr, or a combination thereof, B' includes W, Mo, Cr, Ta, Nb, Ti, or a combination thereof, $1 \leq m \leq 2$, $n \geq 1$, $0 \leq d \leq 1$, and $n-1-d \geq 0$.

The two-dimensional layered material may include a layered metal oxide including a first layer having a positive charge and a second layer having a negative charge which are laminated, a monolayer nanosheet exfoliated from the layered metal oxide, a nanosheet laminate of the monolayer nanosheets, or a combination thereof.

The two-dimensional layered material may cover an entire surface of at least one of the crystal grains.

The cationic compound may include a (C1 to C16 alkyl) ammonium compound, a (C1 to C16 alkyl)amine compound, or a combination thereof.

The two-dimensional layered material may be present in an amount of about 10 volume % to about 100 volume %, based on 100 volume % of the grain boundary insulation layer.

The crystal grains may include barium titanate, strontium titanate, lead titanate, lead zirconate, lead zirconate titanate, or a combination thereof.

The crystal grains may have an average particle diameter of about 50 nm to about 1.5 µm.

According to an embodiment, an electronic device includes the dielectric device.

The electronic device may be a varistor, a thermistor, or an energy storage capacitor.

The dielectric constant of the dielectric material according to an embodiment, including a two-dimensional layered device, does not decrease below a predetermined level even if the thickness is decreased and thus an ultra-thin film may be available, e.g., used.

When applied to a dielectric device such as an intergranular insulation layer capacitor, and the like, an ultra-thin film may be available and a limit of a comparative intergranular insulation type capacitor may be overcome.

The dielectric material including the two-dimensional layered device may be manufactured using a simple method.

BRIEF DESCRIPTION OF THE DRAWINGS

The above and other advantages and features of this disclosure will become more apparent by describing in further detail exemplary embodiments thereof with reference to the accompanying drawings, in which.

DETAILED DESCRIPTION

Figure 1:
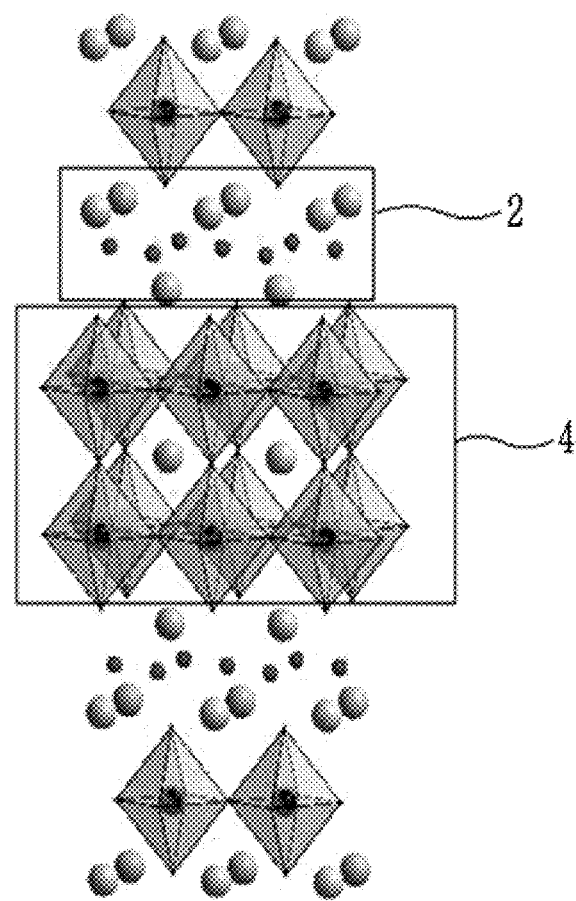
FIG. 1 schematically shows a crystal structure of a two-dimensional layered material when d=0 in Chemical Formula 1 of an dielectric material according to an embodiment, FIG. 2 schematically shows a crystal structure of a two-dimensional layered material when d=1 in Chemical Formula 1 of an dielectric material according to an embodiment, FIG. 3 schematically shows a structure of a first layer substituted with protons ($H^+$) in a two-dimensional layered material according to an embodiment, FIG. 4 schematically shows a structure wherein at least one portion of protons ($H^+$) of a first layer is substituted with a cationic polymer in a two-dimensional layered material according to an embodiment, FIG. 5 schematically shows a nanosheet monolayer structure in which a cationic compound, e.g., a polymer, is attached to a surface of a two-dimensional layered material according to an embodiment, FIG. 6 schematically shows a dielectric device according to an embodiment, FIG. 7 sequentially shows a process of exfoliating a monolayer nanosheet from a layered metal oxide in a method of manufacturing a dielectric material according to an embodiment.

Advantages and characteristics of this disclosure, and a method for achieving the same, will become evident referring to the following example embodiments together with the drawings attached hereto. However, the embodiments should not be construed as being limited to the embodiments set forth herein. If not defined otherwise, all terms (including technical and scientific terms) in the specification may be defined as commonly understood by one skilled in the art. The terms defined in a generally-used dictionary may not be interpreted ideally or exaggeratedly unless clearly defined. In addition, unless explicitly described to the contrary, the word "comprise" and variations such as "comprises" or "comprising", will be understood to imply the inclusion of stated elements but not the exclusion of any other elements.

Further, the singular includes the plural unless otherwise defined.

In the drawings, the thickness of layers, films, panels, regions, etc., are exaggerated for clarity. Like reference numerals designate like elements throughout the specification.

It will be understood that when a first element such as a layer, film, region, or substrate is referred to as being "on" second element, it can be directly on the other element or intervening elements may also be present. In contrast, when an element is referred to as being "directly on" another element, there are no intervening elements present.

It will be understood that when a first element is referred to as being on a second element, the first element and the second element are adjacent to each other (e.g., being contacted to each other), but the upper or lower position is not limited.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region,"

"layer" or "section" discussed below could be termed a second element, component, region, layer or section without departing from the teachings herein.

The terminology used herein is for the purpose of describing particular embodiments only and is not intended to be limiting. "At least one" is not to be construed as limiting "a" or "an." "Or" means "and/or." As used herein, the term "and/or" includes any and all combinations of one or more of the associated listed items.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, unless otherwise defined, a "two-dimensional layered material" refers to a material having a two-dimensional crystal structure which is a material, e.g., a sheet or film including one or more layered structures, e.g., 1 to 9 atomic layers.

According to an embodiment, a dielectric material may include a two-dimensional layered material having a two-dimensional crystal structure.

The two-dimensional layered material according to an embodiment may include a layered metal oxide including a first layer having a positive charge and a second layer having a negative charge which are laminated, a monolayer nanosheet exfoliated from the layered metal oxide, a nanosheet laminate of the monolayer nanosheets, or a combination thereof.

In other words, the two-dimensional layered material according to an embodiment may be a layered metal oxide, a monolayer nanosheet exfoliated from the layered metal oxide, or a laminate of two or more monolayer nanosheets, which may be intermixed.

A two-dimensional layered material according to an embodiment may be represented by Chemical Formula 1

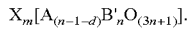    Chemical Formula 1

In Chemical Formula 1, X includes H, $Bi_2O_2$, a cationic compound, or a combination thereof, A includes Bi, Ba, Ca, Pb, Sr, or a combination thereof, B' includes W, Mo, Cr, Ta, Nb, Ti, or a combination thereof, $1 \le m \le 2$, $n \ge 1$, $0 \le d \le 1$, and $n-1-d \ge 0$.

According to an embodiment, Chemical Formula 1 may be divided into a positive-charged moiety $X_m$ and a negative-charged moiety $[A_{(n-1-d)}B'_nO_{(3n+1)}]$.

The two-dimensional layered material according to an embodiment may include a first layer including $X_m$ and a second layer including $[A_{(n-1-d)}B'_nO_{(3n+1)}]$, and may have a laminate structure including the first layer and the second layer, e.g., a laminate structure including alternating first and second layers, so the two-dimensional layered material exhibits electrical neutrality, when viewed as a whole.

In an embodiment, a second layer 4 has a two-dimensional crystal structure formed by metal elements in an A position and in a B position together with an oxygen atom. A two-dimensional layered material according to an embodiment may include a two-dimensional crystal structure in the second layer 4.

The second layer 4 may exhibit a different two-dimensional crystal structure depending upon a mole ratio of metal elements positioned in the A position and the B position.

Figure 2:
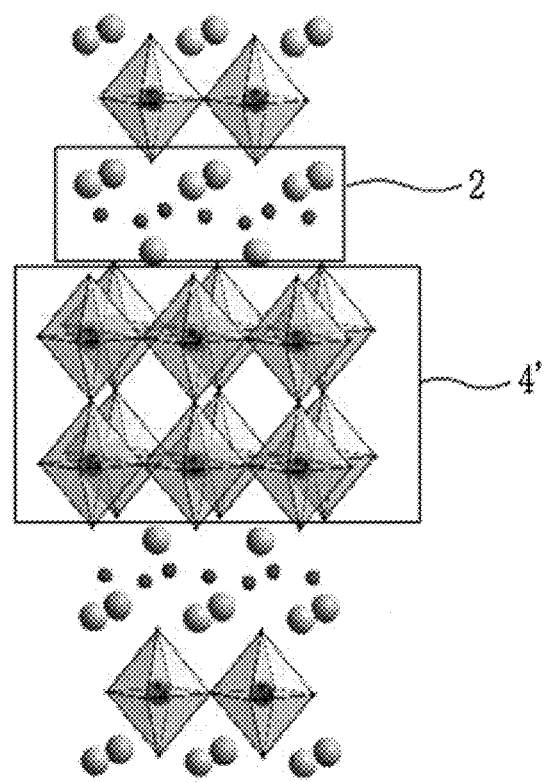

FIG. 1 schematically shows a portion of a consecutive crystal structure of a two-dimensional layered material when d=0 in Chemical Formula 1 and FIG. 2 schematically shows a portion of a consecutive crystal structure of a two-dimensional layered material when d=1 in Chemical Formula 2. In FIGS. 1 and 2, X may be $Bi_2O_2$ and n may be 2.

Referring to FIGS. 1 and 2, the second layer 4 may have a two-dimensional crystal structure represented by $[A_{(n-1)}B'_nO_{(3n+1)}]$ as shown in FIG. 1 and a second layer 4' may have a two-dimensional crystal structure represented by $[A_{(n-2)}B'_nO_{(3n+1)}]$ having a defect in the A position as shown in FIG. 2.

For example, when the two-dimensional layered material is a layered metal oxide as shown in FIGS. 1 and 2, the two-dimensional layered material may include a structure in which the first layer 2 and the second layer 4 are alternated three times or more and laminated, e.g., the first layer 2 and the second layer 4 include three or more laminated layers, for example, a crystal structure having a Aurivillius phase or a layered perovskite crystal structure that is similar thereto.

A crystal structure of the two-dimensional layered material according to an embodiment is not limited to the crystal structure shown in FIG. 1 or 2, but may be in a range satisfying $n-1-d \ge 0$, and may include all crystal structures including laminated alternating first and second layers.

The second layer 4 may include at least two different metal elements in each of a position A and a position B in Chemical Formula 1. In other words, when Bi is for example positioned in the position A of Chemical Formula 1, Ba, Ca, Pb, Sr, or a combination thereof may be further doped within a range satisfying a mole ratio (n−1−d) of the position A.

Figure 3:
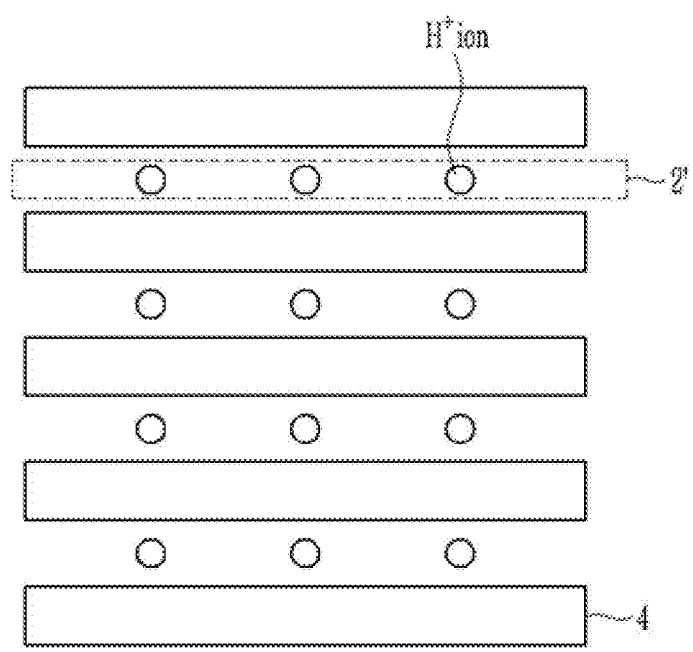
Figure 4:
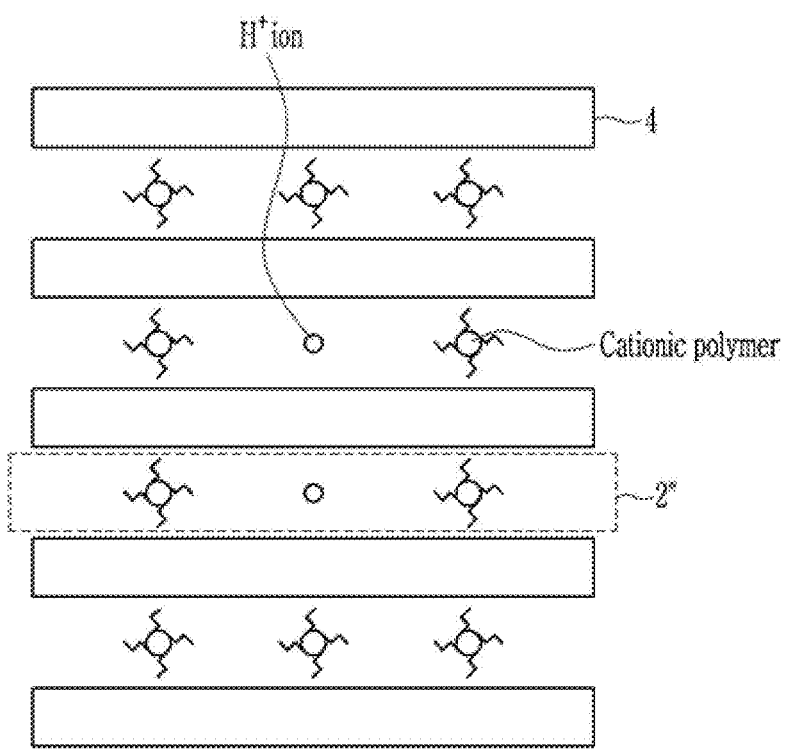

FIG. 3 schematically shows a structure of a first layer 2' substituted with protons (H+) in a two-dimensional layered material according to an embodiment and FIG. 4 schematically shows a structure wherein at least one portion of protons (H+) of a first layer 2'' is substituted with a cationic compound, e.g. a polymer in a two-dimensional layered material according to an embodiment.

In a two-dimensional layered material according to an embodiment, the first layers 2, 2', and 2'' which may be bond layer connecting, e.g., between, adjacent second layers 4 may include $Bi_2O_2$ or may be a layer in which the $Bi_2O_2$ is substituted with protons (H+ ions) or a cationic compound, e.g. a polymer.

For example, the two-dimensional layered material may be a laminate of a first layer 2 and a second layer 4 alternating three times or more as shown in FIG. 1 or 2, wherein the first layer may include a layered metal oxide including f $Bi_2O_2$.

When $Bi_2O_2$ of the first layer 2 of the layered metal oxide are replaced by protons, the first layer 2' may become an assembly layer of protons as shown in FIG. 3. When at least one of the protons is replaced by a cationic compound, e.g., a cationic polymer, the first layer 2″ may become an assembly layer of protons and a cationic compound, e.g. a polymer, or an assembly layer of a cationic compound, e.g. a polymer as shown in FIG. 4.

In an embodiment, when the first layer 2 includes $Bi_2O_2$, the first layer 2 may have a two-dimensional crystal structure. When the first layer 2 is substituted with a proton or a cationic compound, e.g. a polymer except $Bi_2O_2$, substituted first layers 2' and 2″ may not have a two-dimensional crystal structure.

In an embodiment, the cationic compound, e.g. a polymer is attached to the surface of the second layer 4 and also has a size of greater than or equal to the interlayer distance of adjacent second layers 4. In other words, the cationic compound, e.g. a polymer may be an intercalant interposing between second layers 4 and widening a gap between second layers 4 to separate layers.

The cationic compound is not particularly limited as long as the cationic compound has a size greater than or equal to the interlayer distance between adjacent second layers 4 and functions as an intercalant. The cationic compound as used herein includes polymers, and may be positively charged or capable of being positively charged under the conditions of use. The cationic compound may include, for example, a (C1 to C16 alkyl)ammonium compound, a (C1 to C16 alkyl) phosphonium compound, a (C1 to C16 alkyl)amine compound, an amine polymer, or a combination thereof. The alkylamine compound may be a primary, secondary, or tertiary amine.

Non-limiting examples of the alkyl ammonium may be tetramethylammonium (TMA), tetraethylammonium (TEA), tetrapropylammonium (TPA), tetrabutylammonium (TBA), and non-limiting examples of the alkylamine may be methylamine (MA), ethylamine (EA), propylamine (PA), butylamine (BA), and the like, but are not limited thereto.

Figure 5:
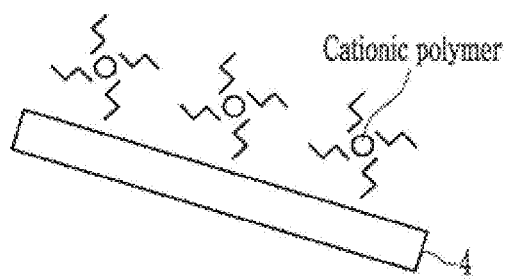

FIG. 5 schematically shows a nanosheet monolayer structure in which a cationic compound, e.g. a polymer is attached to a surface of the nanosheet monolayer structure in a two-dimensional layered material according to an embodiment.

A two-dimensional layered material according to an embodiment may include a monolayer nanosheet.

The second layer 4 may have a negative charge, but the cationic compound, e.g. a polymer may have a positive charge, and the monolayer nanosheet may include a cationic compound, e.g. a polymer attached to the surface in order to maintain electrical neutrality.

The monolayer nanosheet has a structure in which the cationic compound, e.g. a polymer is attached to the surface of the second layer 4 as shown in FIG. 5. The monolayer nanosheet may be obtained by substituting $Bi_2O_2$ of the first layer 2 with a proton as shown in FIG. 3, substituting the same with a cationic compound, e.g. a polymer as shown in FIG. 4, and exfoliating the same.

The two-dimensional layered material according to an embodiment may include a nanosheet laminate in which two or more monolayer nanosheets are laminated.

The nanosheet laminate according to an embodiment includes both the monolayer nanosheet being incompletely separated as a monolayer so as to provide two or more layers and the preliminarily separated monolayer nanosheets being laminated and including two or more layers.

When the monolayer nanosheets are laminated and include two or more layers, the dielectric material according to an embodiment may further include a binder for binding, e.g., between, adjacent monolayer nanosheets.

Non-limiting examples of the binder according to an embodiment may be methyl cellulose, ethyl cellulose, hydroxypropyl methyl cellulose (HPMC), hydroxypropyl cellulose (HPC), xanthan gum, polyvinyl alcohol (PVA), polyvinyl pyrrolidone (PVP), carboxy methyl cellulose, hydroxyethyl cellulose, or a combination thereof. A content of the binder may be appropriately selected, but is not particularly limited.

The two-dimensional layered material according to an embodiment may have an average longitudinal diameter of greater than or equal to about 0.1 μm, for example greater than or equal to about 0.5 μm, greater than or equal to about 1 μm, greater than or equal to about 2 μm, greater than or equal to about 3 μm, greater than or equal to about 4 μm, greater than or equal to about 5 μm, or greater than or equal to about 6 μm. The longitudinal diameter as used herein refers to a longitudinal length when the crystal grain has a shape of oval or a uniaxially elongated shape similar to an oval such as a needle, a diameter length in the case of a circle/spherical shape, or a farthest distance of a line connecting any two points in the crystal grain boundary in the case of a polygonal or amorphous shape.

The two-dimensional layered material may have an average longitudinal diameter of less than or equal to about 100 μm, for example, less than or equal to about 90 μm, less than or equal to about 80 μm, less than or equal to about 70 μm, less than or equal to about 60 μm, less than or equal to about 50 μm, less than or equal to about 40 μm, less than or equal to about 30 μm, less than or equal to about 20 μm, less than or equal to about 10 μm, less than or equal to about 9 μm, less than or equal to about 8 μm, less than or equal to about 7 μm, less than or equal to about 6 μm, or less than or equal to about 5 μm.

The two-dimensional layered material may have an average thickness of less than or equal to about 100 nm, less than or equal to about for example 90 nm, less than or equal to about 80 nm, less than or equal to about 70 nm, less than or equal to about 60 nm, less than or equal to about 50 nm, less than or equal to about 40 nm, less than or equal to about 30 nm, less than or equal to about 20 nm, less than or equal to about 10 nm, less than or equal to about for example, 5 nm, less than or equal to about 3 nm, less than or equal to about 2.5 nm, or less than or equal to about 2 nm. The two-dimensional layered material may have an average thickness of greater than or equal to about 1 nm.

The two-dimensional layered material according to an embodiment may provide a dielectric material having an ultra-thin film and improved dielectric characteristics relative to a comparative dielectric material, by adjusting the average longitudinal diameter and the average thickness of the monolayer nanosheet according to an embodiment within the previously disclosed ranges.

A dielectric material according to an embodiment may have a relative density of about 50% to about 90%, for example about 60% to about 90%, about 65% to about 90%, about 70% to about 90%, about 75% to about 90% and may have a dielectric constant of greater than about 50, for example, greater than or equal to about 60, greater than or equal to about 70, greater than or equal to about 80, greater than or equal to about 90, or greater than or equal to about 100.

A dielectric material according to an embodiment may show an excellent dielectric constant due to internal pores even if the relative density is relatively low.

$BaTiO_3$ which may be used as a dielectric material has a three-dimensional crystal structure. A core of $BaTiO_3$ is formed with a three-dimensional tetragonal crystal structure having a large dielectric constant, and the surface is formed with a three-dimensional cubic crystal structure having a low dielectric constant (low-k), so a fraction of the three-dimensional cubic crystal structure of the surface may be increased when a thickness of the dielectric material is decreased. Accordingly, a comparative dielectric material tends to decrease the dielectric constant according to decreasing the thickness of the dielectric material.

A dielectric material according to an embodiment has a two-dimensional crystal structure including, e.g., caused by, the second layer 4 of the two-dimensional layered material. Such a two-dimensional crystal structure may be formed in very thin thickness of several to several hundred nanometers, for example, several nanometers to several tens of nanometers, and also may maintain the inherent crystal structure regardless of the thickness decrease, so such a two-dimensional crystal structure may be very suitable for forming an ultra-thin film and improving dielectric characteristics relative to a comparative dielectric material.

Hereinafter, a dielectric device including the dielectric material is described.

Figure 6:
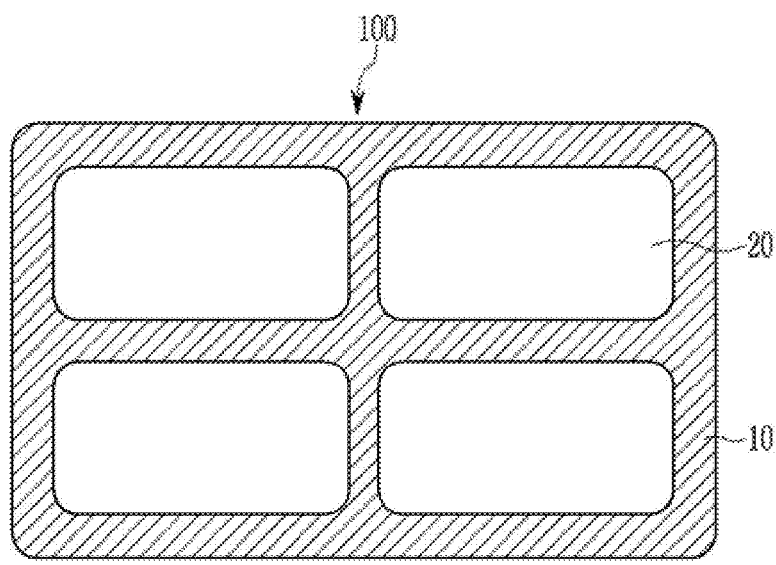

FIG. 6 schematically shows a dielectric device according to an embodiment.

A dielectric device 100 according to an embodiment may include a plurality of crystal grains 20 including a material having semi-conductivity or conductivity e.g., a semiconductor or conductive material, and a grain boundary insulation layer 10 between the crystals grains, e.g., surrounding at least one of the crystal grains 20 or surrounding boundaries of the crystal grains 20, wherein the grain boundary insulation layer 10 covers at least a portion of the surface of the crystal grains and also includes a dielectric material including the two-dimensional layered material.

The dielectric device 100 according to an embodiment may be an intergranular insulation type capacitor which provides a capacitance in the grain boundary insulation layer 10 formed between the two crystal grains 20 when a predetermined voltage is applied to two adjacent crystal grains 20, so as to function as a capacitor.

In addition, the plurality of crystal grains and grain boundaries are connected with each other in serial and/or in parallel, so as to carry out the overall functions of the capacitor having a predetermined capacitance.

Referring to FIG. 6, crystal grains 20 may be disposed in a plurality. A plurality of crystal grains 20 may be formed of a material having semi-conductivity or conductivity, i.e., the material may be a semiconductor or conductive material. A material of the crystal grains 20 may be, for example, a metal oxide including barium titanate, strontium titanate, lead titanate, lead zirconate, lead zirconate titanate, or a combination thereof.

According to an embodiment, a donor element may be further included in the material for the crystal grains 20. The metal oxide for the crystal grains 20 may have an oxygen vacancy, and the donor element may be incorporated, e.g., solid-dissolved, in the crystal grains 20. Accordingly, the crystal grains 20 may become semi-conductive. Examples of the donor element may include La, Sm, Dy, Ho, Y, Nd, Ce, Nb, Ta, W, and the like.

According to an embodiment, the average particle diameter of the crystal grains 20 may be varied or variously determined taking into account or considering an apparent dielectric constant of the dielectric device 100, but may be adjusted within the suitable range for down-sizing and providing a film with a reduced thickness in the dielectric device 100.

An average particle diameter of the crystal grains 20 may be for example less than or equal to about 1.5 µm, less than or equal to about 1.4 µm, less than or equal to about 1.3 µm, less than or equal to about 1.2 µm, less than or equal to about 1.1 µm, less than or equal to about 1.0 µm, less than or equal to about 900 nm, less than or equal to about 800 nm, less than or equal to about 700 nm, less than or equal to about 600 nm, or less than or equal to about 500 nm and may be for example greater than or equal to about 50 nm, greater than or equal to about 60 nm, greater than or equal to about 70 nm, greater than or equal to about 80 nm, greater than or equal to about 90 nm, or greater than or equal to about 100 nm.

The grain boundary insulation layer 10 includes the dielectric material. An amount of the two-dimensional layered material, e.g., a ratio of the two-dimensional layered material to the three-dimensional bulk material, in the grain boundary insulation layer 10 is not particularly limited but may be varied or variously determined taking into account or considering a dielectric constant of other materials, for example, a three-dimensional bulk material having a three-dimensional crystal structure, a raw material, a thickness when forming the grain boundary insulation layer 10, and the like. But the amount of the two-dimensional layered material in the grain boundary insulation layer 10 may be determined to provide an improved dielectric constant caused by the two-dimensional layered material even when the grain boundary insulation layer 10 is formed in, e.g., with, a size, e.g., thickness, of several nanometers to several tens of nanometers.

An amount of the two-dimensional layered material in the grain boundary insulation layer 10 may be for example greater than or equal to about 10 volume %, greater than or equal to about 15 volume %, greater than or equal to about 20 volume %, greater than or equal to about 25 volume %, greater than or equal to about 30 volume %, greater than or equal to about 35 volume %, for example, greater than or equal to about 40 volume %, greater than or equal to about 45 volume %, greater than or equal to about 50 volume %, greater than or equal to about 55 volume %, greater than or equal to about 60 volume %, greater than or equal to about 65 volume %, greater than or equal to about 70 volume %, greater than or equal to about 75 volume %, greater than or equal to about 80 volume %, greater than or equal to about 85 volume %, greater than or equal to about 90 volume %, greater than or equal to about 95 volume %, or greater than or equal to about 100 volume % based on 100 volume % of the grain boundary insulation layer 10.

The two-dimensional layered material may be directly contacted with the surface of the crystal grains 20, or may be disposed so that at least a portion thereof may leave a space in a predetermined gap from the surface of the crystal grains 20, e.g., an interval of a predetermined distance may be present between the two-dimensional layered material and the surface of the crystal grains 20.

In addition, the two-dimensional layered material may be formed only in a partial region of the surface of the crystal grains 20 to cover a portion of the surface of crystal grains 20, or may be formed to cover the entire surface of at least one of the crystal grains 20.

The dielectric device 100 may have a dielectric constant caused by the two-dimensional crystal structure of the two-dimensional layered material of the grain boundary insulation layer 10. The dielectric constant of the dielectric device 100 according to an embodiment may be varied or variously determined depending upon an average particle diameter of the crystal grain and a thickness of the grain boundary insulation layer, but the dielectric device 100 may have a dielectric constant allowable for a capacitor even if the dielectric device 100 is formed in, e.g., with, a ultra-small size, e.g., including a ultra-thin film.

The dielectric device 100 may have a dielectric constant of, for example, greater than or equal to about 1,000, greater than or equal to about 2,000, greater than or equal to about 3,000, greater than or equal to about 4,000, greater than or equal to about 5,000, greater than or equal to about 6,000, greater than or equal to about 7,000, greater than or equal to about 8,000, greater than or equal to about 9,000, or greater than or equal to about 10,000.

The dielectric device may satisfy the following Equation 1 relating to the apparent dielectric constant.

$$\varepsilon_{rAPP} \square \varepsilon_r \cdot d/t \qquad \text{Equation 1}$$

In Equation 1, $\varepsilon_{rAPP}$ refers to an apparent dielectric constant of a dielectric device, $\varepsilon_r$ refers to a dielectric constant of a grain boundary insulation layer, d refers to an average particle diameter of a crystal grain, and t refers to a thickness of a grain boundary insulation layer.

The intergranular insulation layer, which may be included in comparative dielectric devices, includes only three-dimensional bulk material having a three-dimensional crystal structure such as $BaTiO_3$, and the like, and the apparent dielectric constant of the dielectric device tends to be decreased when a thickness t of the grain boundary insulation layer is decreased. Accordingly, in a comparative dielectric device it may be difficult to form a grain boundary insulation layer in an ultra-thin film having a thickness below a predetermined level.

As the dielectric device according to an embodiment has a two-dimensional crystal structure including at least a two-dimensional layered material, the dielectric device may show a dielectric constant greater than or equal to a predetermined level, e.g., caused by the two-dimensional layered material, even if the grain boundary insulation layer is formed in a ultra-thin film having a thickness t of several nanometers to several tens of nanometers. When using the two-dimensional layered material, a thickness and a dielectric constant of the grain boundary insulation layer may be independently controlled, unlike a comparative dielectric device.

Accordingly, the dielectric device according to an embodiment includes the two-dimensional layered material in the grain boundary insulation layer, and a dielectric constant greater than or equal to a predetermined level caused by the two-dimensional layered material even if the dielectric device is formed in a form of an ultra-thin film having a thickness of several nanometers to several tens of nanometers may be exhibited, and also the device may be formed in a small-size and with a thin-film.

According to an embodiment, an electronic device includes the dielectric device 100. The electronic device may be a device functioning as a variable resistor such as a varistor or a thermistor or an energy storage capacitor.

Hereinafter, a method of manufacturing the dielectric material is described.

Figure 7:
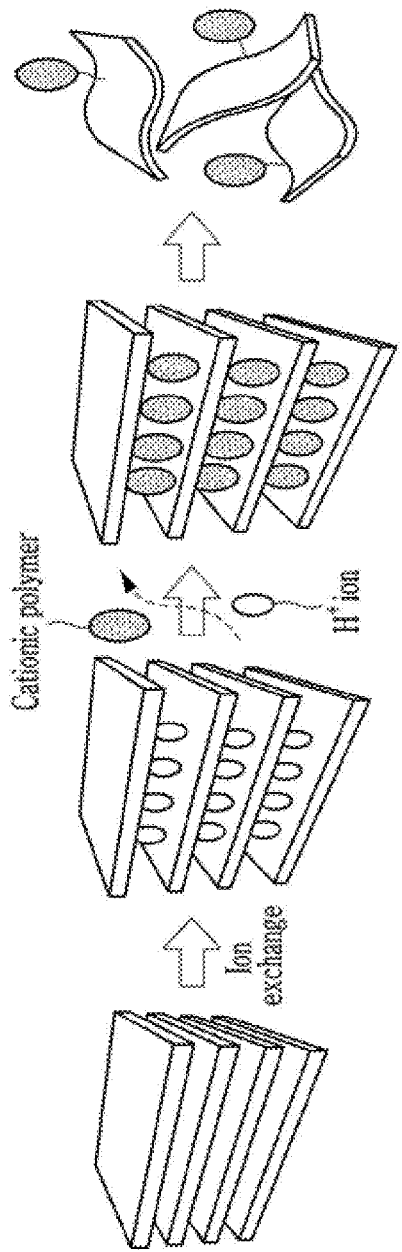

FIG. 7 sequentially shows a process of exfoliating a monolayer nanosheet from a layered metal oxide in a method of manufacturing a dielectric material according to an embodiment Referring to FIG. 7, a method of manufacturing a dielectric material according to an embodiment includes preparing a layered metal oxide including a first layer having a positive charge and a second layer having a negative charge which are alternated and laminated, acid-treating the layered metal oxide to exchange the first layer with protons, colloidizing the acid-treated layered metal oxide to replace the protons by cationic compounds, e.g. polymers, and exfoliating the monolayer nanosheet including the second layer from the colloidized layered metal oxide.

Hereinafter, the process of exfoliating the layered metal oxide of $Bi_2O_2[W_2O_7]$ into $TBA\text{-}[W_2O_7]$ monolayer nanosheets further referring to FIGS. 8 to 13 in addition to FIG. 7. FIGS. 8 to 13 show one example of the method of manufacturing a dielectric material according to an embodiment, but an embodiment is not limited to the layered metal oxide or the used cationic compound, e.g. a polymer.

Figure 8:
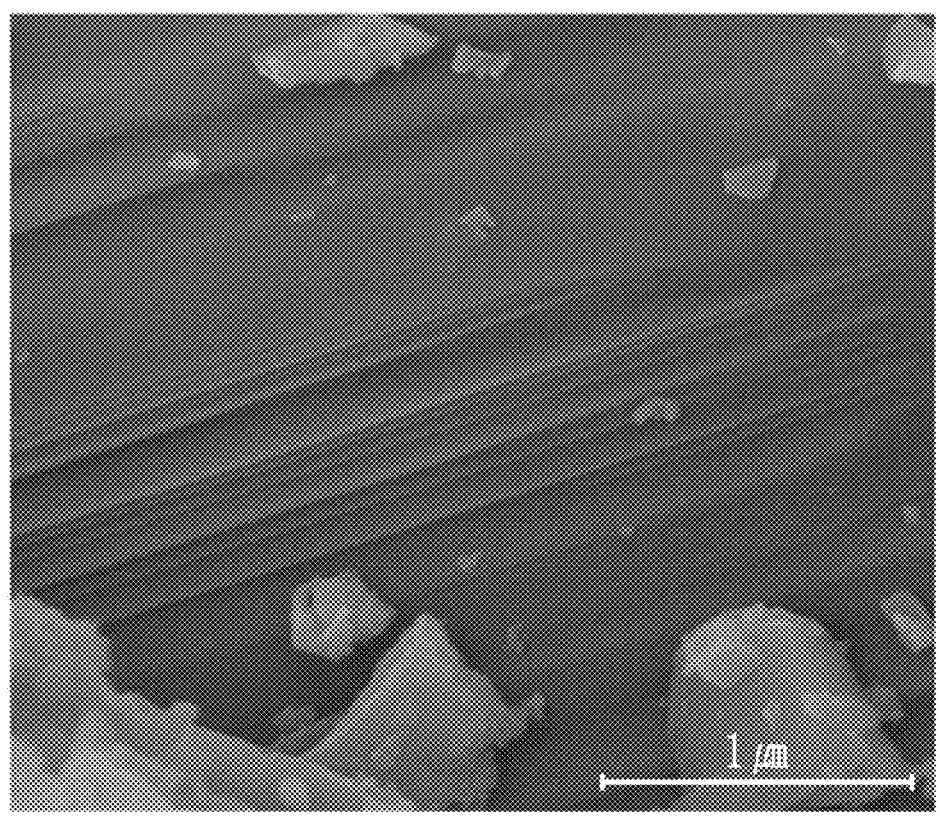
FIG. 8 is a microscopic image of a layered metal oxide $Bi_2O_2[W_2O_7]$ according to an embodiment.

FIG. 8 is a microscopic image showing a layered metal oxide $Bi_2O_2[W_2O_7]$ according to an embodiment.

First, as shown in FIG. 8, a layered metal oxide in which a first layer ($Bi_2O_2$) and a second layer ($W_2O_7$) are alternated and laminated several times is prepared.

Figure 9:
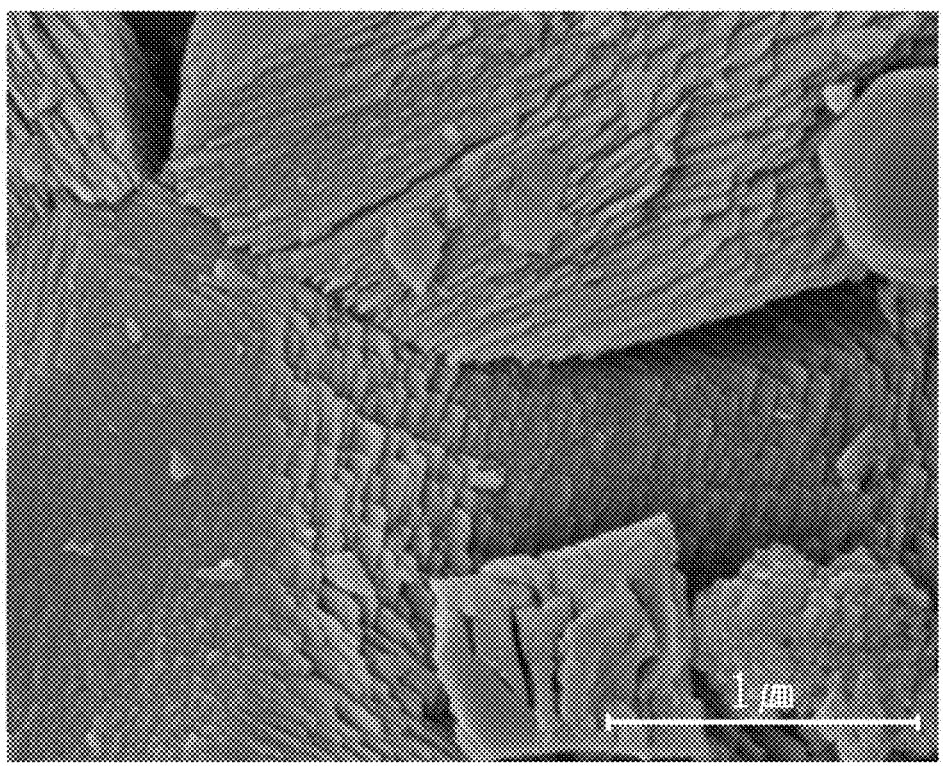
FIG. 9 is a microscopic image of $H_2[W_2O_7]$ in which the layered metal oxide of FIG. 8 is substituted with protons ($H^+$)

FIG. 9 is a microscopic image showing $H_2[W_2O_7]$ in which the layered metal oxide of FIG. 8 is substituted with protons ($H^+$).

Subsequently, the layered metal oxide is reacted with an acidic solution such as HCl, $HNO_3$ and the like to make the cationic first layer protonized. In other words, $Bi_2O_2$ of the first layer is ion-exchanged with protons to make the first layer into an assembly layer including protons. Accordingly, the layered metal oxide may become a proton-type layered metal oxide represented by $H_2[W_2O_7]$.

Figure 10:
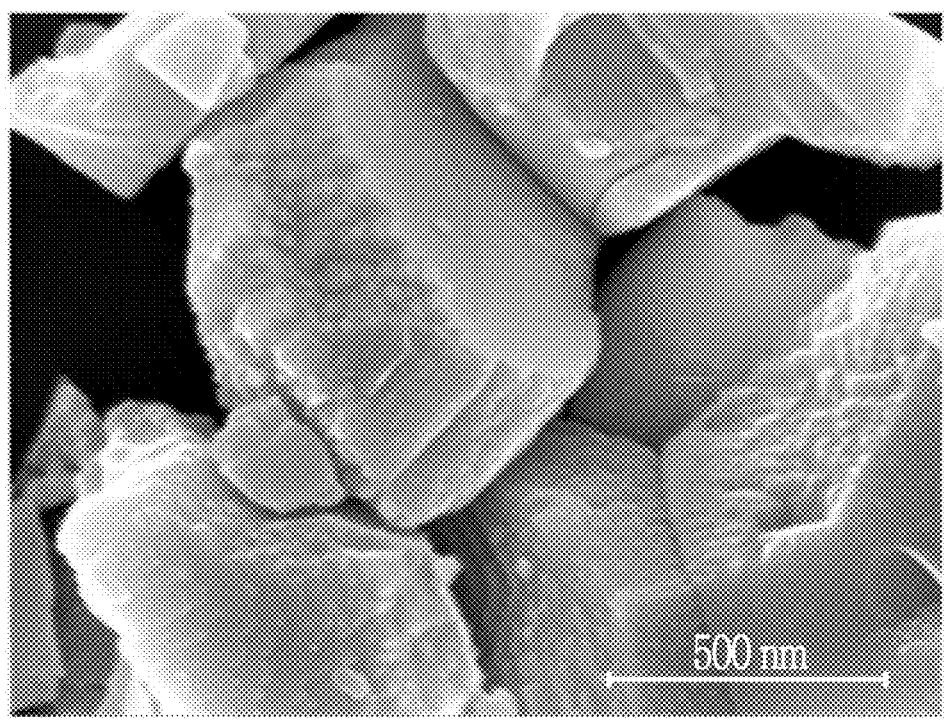
FIG. 10 is a microscopic image of colloidal $H_2[W_2O_7]$ in which $H_2[W_2O_7]$ of FIG. 9 is colloidized.

FIG. 10 is a microscopic image showing colloidal $H_2[W_2O_7]$ in which $H_2[W_2O_7]$ of FIG. 9 is colloidized.

Then, the obtained proton-type layered metal oxide is reacted with a cationic compound, e.g. a polymer to provide a colloid as shown in FIG. 10. Examples of the cationic compound may be a tetramethylammonium compound, a tetraethylammonium compound, a tetrapropylammonium compound, a tetrabutylammonium compound, a methylamine compound, an ethylamine compound, a propylamine compound, a butylamine compound, or a combination thereof. Thereby, at least a portion of protons of the first layer may be substituted with a cationic compound, e.g. a polymer.

As the cationic compound, e.g. a polymer has a large molecule size, the cationic compound, e.g. a polymer may be interposed between adjacent second layers to widen a gap between the second layers, inducing a separation of layers.

Two or more kinds of cationic compounds, e.g. polymers having different sizes from each other may be used during substituting the cationic polymer. For example, the two or more kinds of cationic compounds having different sizes from each other may be two or more kinds of compounds having different sizes by having different carbon numbers of alkyl groups or different functional groups from each other.

When two or more kinds of cationic compounds, e.g. polymers are used as above, the two or more kinds of cationic compounds may be present on the surface of the prepared monolayer nanosheet.

Without wishing to being bound by any particular theory, it may be difficult to uniformly exfoliate into a monolayer when using only one kind of cationic compound, e.g. polymer having a predetermined size during the exfoliation process using a cationic compound, e.g. polymer. For example, when a single cationic compound such as a tetrabutylammonium salt compound (e.g., tetrabutylammonium hydroxide, hereinafter TBAOH) or a tetramethylammonium compound (e.g., tetramethylammonium hydroxide, hereinafter TMAOH) is used, it may be difficult to exfoliate the protonized layered metal oxide into monolayers but may be exfoliated into a sheet having two or more layers with a random thickness, and the obtained nanosheets may have an average thickness of about 3 nm to about 4 nm.

In an embodiment, the layered metal oxide to be exfoliated may be treated with a mixture of a small-sized cationic compound, e.g., polymer and a large-sized cationic compound, e.g., polymer, but is not limited thereto.

Figure 11:
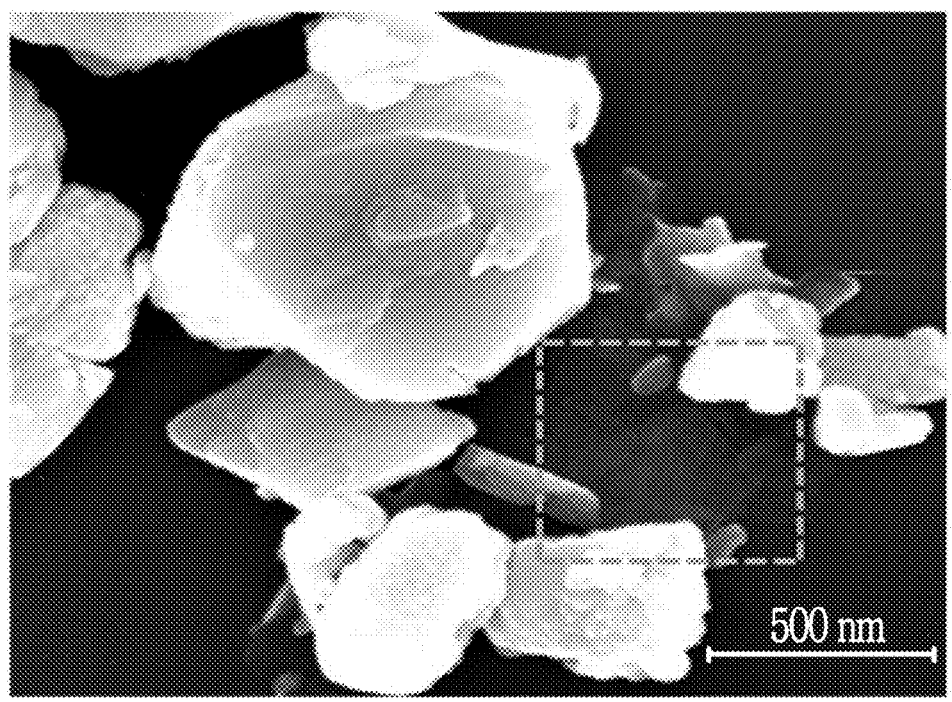
FIG. 11 is a microscopic image of an exfoliated colloidized layered metal oxide and an exfoliated monolayer nanosheet which are mixed.
Figure 12:
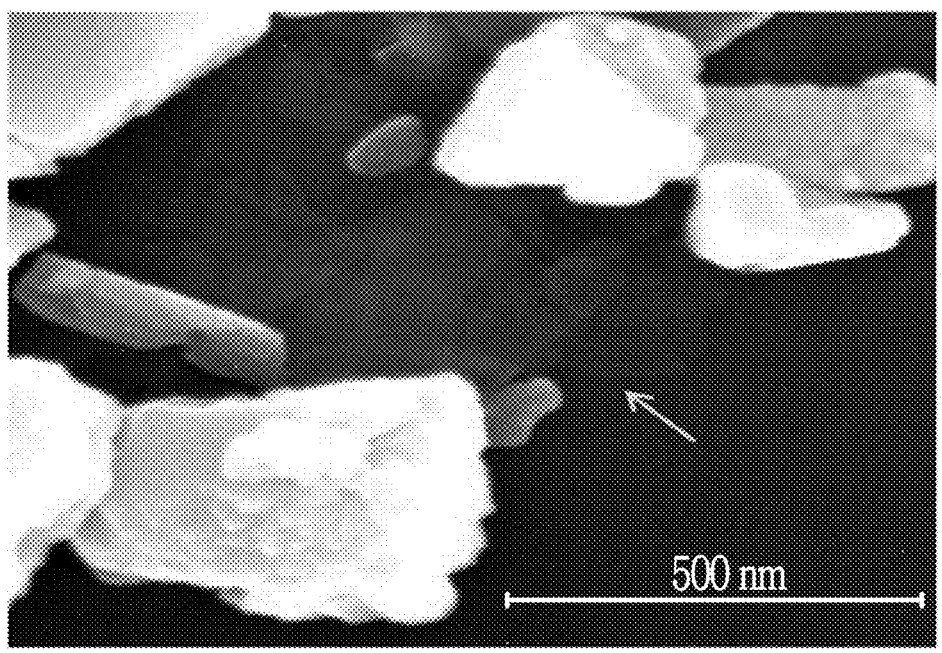
FIG. 12 is an enlarged microscopic image of a region indicated by a dotted line in FIG. 11.

FIG. 11 is a microscopic image showing an exfoliated colloidized layered metal oxide and an exfoliated monolayer nanosheet which are mixed and FIG. 12 is an enlarged microscopic image of a region indicated by a dotted line in FIG. 11.

Then, the layered metal oxide colloidized by cationic compounds, e.g., polymers is added into a solvent and stirred to exfoliate a monolayer nanosheet from the colloidized layered metal oxide.

The stirring may include ultrasonication. For example, the cationic compound, e.g., polymer may be inserted by stirring for a predetermined time and performed with ultrasonication. The ultrasonic power may be greater than or equal to about 20 watts (W), for example, greater than or equal to about 40 W, or greater than or equal to about 60 W. The ultrasonic power may be less than or equal to about 400 W, for example, less than or equal to about 300 W, less than or equal to about 200 W, or less than or equal to about 100 W. The means for ultrasonication may include any disclosed devices or commercially available devices.

The stirring time is not particularly limited and may be appropriately selected. For example, the stirring time may be greater than or equal to about 10 minutes, greater than or equal to about 30 minutes, or greater than or equal to 1 hour. The stirring time may be greater than or equal to about 1 day, greater than or equal to about 2 days, or even greater than or equal to about 3 days. The ultrasonication stirring may shorten the stirring time. The ultrasonication time may be greater than or equal to about 1 minute, for example, greater than or equal to about 5 minutes. The ultrasonication time may be less than or equal to about 300 minutes, for example, less than or equal to about 100 minutes, less than or equal to about 90 minutes, less than or equal to about 80 minutes, less than or equal to about 70 minutes, or less than or equal to about 60 minutes.

The monolayer nanosheets obtained by the ultrasonication may exhibit a relatively low deviation in a lateral size. Thus, according to an embodiment, the monolayer nanosheets may exhibit a standard deviation of less than or equal to about 1.5 μm, for example, less than or equal to about 1 μm, less than or equal to about 0.9 μm, less than or equal to about 0.8 μm, less than or equal to about 0.7 μm, less than or equal to about 0.6 μm, or less than or equal to about 0.5 μm in a lateral size.

When the monolayer nanosheets are exfoliated by ultrasonication, it may be relative easy to control a concentration of the obtained colloid solution compared to simple stirring. According to an embodiment, the concentration of the monolayer nanosheets in the colloid solution may be about 1 grams per liter (g/L) to about 1.7 g/L, for example, about 1.3 g/L to about 1.6 g/L.

The colloidized layered metal oxide and the nanosheets (arrow parts of FIG. 12) may be mixed even if exfoliation is completed as shown in FIGS. 11 and 12. The nanosheets may include a second layer and a cationic compound, e.g., a polymer, wherein the cationic compound is attached to the surface of the second layer. For example, in FIGS. 11 and 12, the monolayer nanosheets may be shown as a structure such as a "cationic compound-$[A_{(n-1-d)}B'_nO_{3n+1}]$".

Then, the exfoliated monolayer nanosheet may be post-processed to provide, e.g., form, powder or processed to be provided in a shape of pellet and the like, or processed into a shape of a coating agent or the like and a C1 to C15 alcohol, a binder, and selectively a dispersing agent (e.g., C2 to C20 organic acid) may be mixed in a colloidal aqueous solution including the obtained monolayer nanosheet.

According to the method of manufacturing the dielectric material of an embodiment, the layered metal oxide may be exfoliated in a single nanosheet by the simple process, so a dielectric material including the exfoliated single nanosheet may exhibit a high dielectric constant even in the region having a thickness ranging from several nanometers to several tens of nanometers.

Hereinafter, the embodiments are illustrated in more detail with reference to examples. These examples, however, are not in any sense to be interpreted as limiting the scope of the present disclosure.

EXAMPLES

Measurement Method

Apparent Density

Apparent density of obtained powders is measured in an Archimedes method. Herein, the Archimedes method is a method of measuring the apparent density according to Equation 2.

Apparent density=(Dried weight)/(Saturated weight−Suspended weight)*(Water density at a measurement temperature)   Equation 2

Herein, in the above Chemical Formula, the "dried weight" is obtained by drying a specimen and measuring its weight at room temperature (about 25° C.), the "saturated weight" is obtained by putting the specimen in water, boiling it at about 100° C. to fill pores of the specimen with the water, and weighing its weight, and the "suspended weight" is a weight of the specimen measured in the water.

Relative Density

Relative density is calculated according to Equation 3.

Relative density (%)=(Apparent density)/(Theoretical density)*100   Equation 3

Dielectric Constant

A dielectric constant of Examples and Comparative Examples is measured through a dielectric analysis.

A measurement subject powder is molded into a pellet and then, mounted between two electrodes (a dielectric sensor), and a voltage of 1 volt (V) having a wavelength of about 1 kHz is applied to one electrode. Herein, a wavelength transferred therefrom is measured at the other electrode.

A transferred signal has reduced amplitude due to movement of ions and alignment of polarity and thus a phase movement. When a material has polarity, an electric field is realigned, and ions having a charge move toward an electrode having opposite polarity. The measured amplitude and the phase change are used to calculate characteristics of a dielectric material such as a dielectric constant and a loss coefficient.

Subsequently, dielectric constant data of Examples and Comparative Example are respectively divided by a vacuum dielectric constant $\varepsilon_0$ to calculate a dielectric constant of each powder.

Preparation Example: Preparation of TMA-[$W_2O_7$] Nanosheet $Bi_2O_3$ and $WO_3$ are mixed in a mole ratio of 1:2, and the mixture is molded into a pellet. 5 grams (g) of the pellet is put in an alumina crucible and heat-treated in a tube furnace at 600° C. to 900° C. for 10 hours under an oxygen or atmosphere. A total weight of pellet is adjusted in a range of 1 g to 100 g if necessary. Subsequently, the furnace is cooled down to room temperature, and the treated pellet is ground to obtain fine powder.

The obtained fine powder is washed with 100 milliliters (mL) to 1 liter (L) of water for 12 hours and filtered to obtain powder. The powder has a composition of $Bi_2O_2[W_2O_7]$ and a layered structure shown in FIG. 8.

The obtained $Bi_2O_2[W_2O_7]$ powder is added to a 1 molar (M) HCl solution, and the mixture is stirred for 3 days to obtain only powder. The obtained powder has a composition of $H_2[W_2O_7]$ and a layered structure shown in FIG. 9.

Six moles (mols) of a tetramethylammonium oxide (TMAOH) aqueous solution as an intercalant is added to 4 g of the obtained $H_2[W_2O_7]$ powder, and the mixture is stirred for 3 weeks. Herein, a fine structure of the colloidized powder is shown in FIG. 10. Subsequently, 6 mols of a TMAOH aqueous solution is added to the stirred solution, and the obtained mixture is additionally stirred for 4 weeks.

A final solution after all the processes is centrifuged at 2,000 rotations per minute (rpm) for 30 minutes, and floating (excess) TMAOH is removed by using a dialysis tube to obtain an aqueous colloid solution including exfoliated TMA-$[W_2O_7]$ nanosheets. In the aqueous colloid solution, the TMA-$[W_2O_7]$ nanosheets and the colloidized layered metal oxide are mixed as shown in FIGS. 11 and 12.

The layered monolayer nanosheets exfoliated from $Bi_2O_2[W_2O_7]$ have $TMA^+$ ions attached to the surface of a $W_2O_7$ layer having a two-dimensional crystal structure as shown in FIG. 5.

Example 1: $Bi_2O_2[W_2O_7]$ Layered Metal Oxide

A pellet including $Bi_2O_2[W_2O_7]$ layered metal oxide according to Example 1 is obtained by molding the $Bi_2O_2[W_2O_7]$ powder of Preparation Example into a pellet and heat-treating the pellet at 800° C.

Example 2: $H_2[W_2O_7]$ Proton-type Layered Metal Oxide

A pellet including $H_2[W_2O_7]$ proton-type layered metal oxide according to Example 2 is obtained by acid-treating the $Bi_2O_2[W_2O_7]$ powder of Preparation Example, molding $H_2[W_2O_7]$ powder obtained therefrom into a pellet, and heat-treating the pellet at 800° C. to 900° C.

The $H_2[W_2O_7]$ proton-type layered metal oxide of Example 2 tends to exhibit increasing relative density, as a heat treatment temperature of the $H_2[W_2O_7]$ pellet is increased (800° C., 850° C., 900° C.).

Example 3: $Bi_2O_2[BiTi_3O_{10}]$ Layered Metal Oxide

A pellet including $Bi_2O_2[BiTi_3O_{10}]$ layered metal oxide according to Example 3 is obtained by mixing $Bi_2O_3$ and $TiO_3$ in a mole ratio of 2:3 in Preparation Example to obtain powder having a composition of $Bi_2O_2[BiTi_3O_{10}]$ instead of the $Bi_2O_2[W_2O_7]$, molding the powder into a pellet, and heat-treating the pellet at 800° C.

Example 4: $Bi_2O_2[BaTa_2O_7]$ Layered Metal Oxide

A pellet including $Bi_2O_2[BaTa_2O_7]$ layered metal oxide according to Example 4 is obtained by mixing $Bi_2O_3$, $Ta_2O_5$, and BaO in a mole ratio of 1:1:1 in Preparation Example to obtain powder having a composition of $Bi_2O_2[BaTa_2O_7]$ instead of the $Bi_2O_2[W_2O_7]$, molding the powder into a pellet, and heat-treating the pellet at 800° C. to 900° C.

The $Bi_2O_2[BaTa_2O_7]$ layered metal oxide of Example 4 tends to exhibit relative density, as a heat treatment temperature of the $Bi_2O_2[BaTa_2O_7]$ pellet is increased (800° C., 850° C.).

Example 5: $H_2[BaTa_2O_7]$ Proton-Type Layered Metal Oxide

A pellet including $H_2[BaTa_2O_7]$ proton-type layered metal oxide according to Example 5 is obtained by putting powder having a composition of $Bi_2O_2[BaTa_2O_7]$ in a 1 M HCl solution, stirring the mixture for 3 days, filtering it to obtain $H_2[BaTa_2O_7]$ powder, molding the powder into a pellet, and heat-treating the pellet at 800° C. to 900° C.

The $H_2[BaTa_2O_7]$ layered metal oxide according to Example 5 tends to exhibit increasing $H_2[BaTa_2O_7]$ layered metal oxide, as a heat treatment temperature of the $H_2[BaTa_2O_7]$ pellet is increased (800° C., 850° C.).

Comparative Example: $BaTiO_3$ 3-Dimensional Bulk Material $BaCO_3$ and $TiO_2$ are mixed in a mole ratio of 1:1, and the mixture is ball-milled to prepare slurry. The slurry is dried through evaporation and then, calcined to obtain $BaTiO_3$ powder according to Comparative Example.

Referring to a FE-SEM analysis result of the $BaTiO_3$ powder, the $BaTiO_3$ pellet is a three-dimensional bulk material having a three-dimensional crystal structure, and the three-dimensional crystal structure has an average thickness of less than 50 nm.

Subsequently, a pellet including $BaTiO_3$ according to Comparative Example is obtained by molding the $BaTiO_3$ powder into a pellet and heat-treating the pellet at 800° C.

Figure 13:
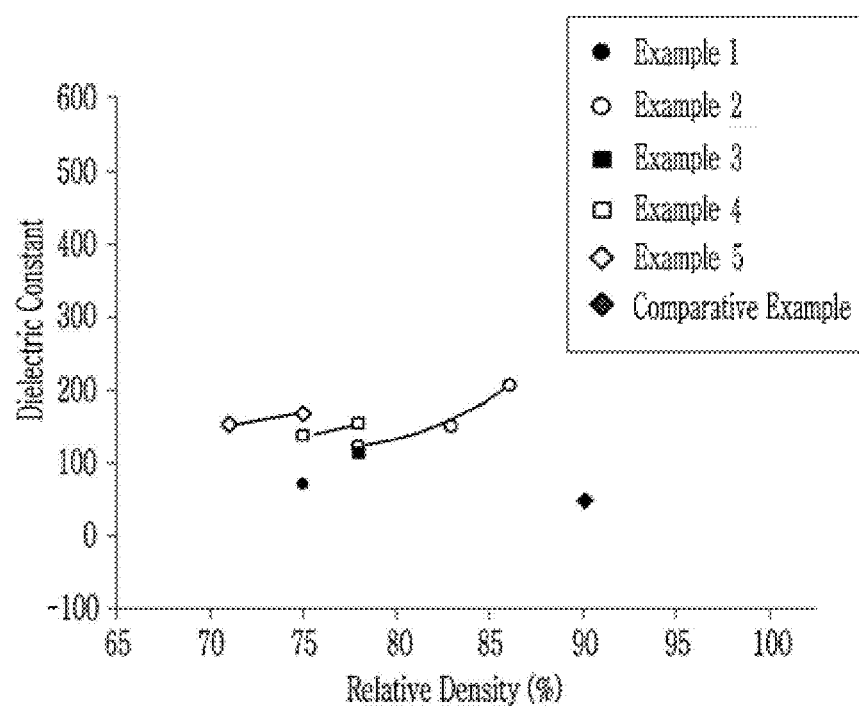
FIG. 13 is a graph showing a dielectric constant at 1 kilohertz (kHz) depending on a relative density (%) of Example 1 to Example 5 and Comparative Example.

Relative density and a dielectric constant of Examples and Comparative Examples are measured according to the above measurement method, and the results are shown in a graph of FIG. 13.

FIG. 13 is a graph showing a dielectric constant at 1 kHz depending on relative density (%) of Examples 1 to 5 and Comparative Example.

In FIG. 13, Example 2 shows gradually increasing relative density, as a heat treatment temperature of the $H_2[W_2O_7]$ pellet is increased up to 800° C., 850° C., and 900° C., and Examples 4 and 5 show increasing relative density when a heat treatment temperature of the $Bi_2O_2[BaTa_2O_7]$ pellet and the $H_2[BaTa_2O_7]$ pellet is increased from 800° C. to 850° C.

Referring to FIG. 13, Examples 1 to 5 show a high dielectric constant as well as low relative density compared with Comparative Examples.

Specifically, Comparative Example shows a dielectric constant of less than 50, that is, about 40 in a relative density region of greater than 90%, Example 1 shows a dielectric constant of about 71 in a relative density region of about 75%, Example 2 shows a dielectric constant of about 120 to about 210 in a relative density region of about 78% to 88%, Example 3 shows a dielectric constant of about 115 in a relative density region of about 78%, Example 4 shows a dielectric constant of about 137 to about 150 in a relative density region of about 75% to about 78%, and Example 5 shows a dielectric constant of about 150 to about 168 in a relative density region of 72% to about 75%.

Comparative Example has relative density of 90% and thus an average thickness of less than 50 nm despite almost no internal pore and accordingly, a relatively low dielectric constant compared with Examples.

In other words, when a dielectric material is manufactured by respectively using Examples 1 to 4, the dielectric material may be formed into a thin layer and have excellent dielectric characteristics compared with Comparative Examples.

Comparing Example 1 with Examples 2, 4, and 5, a first layer including a hydrogen ion has an excellent dielectric constant compared with a first layer including a $Bi_2O_2$ layered metal.

In addition, Example 2 tends to exhibit proportionally increasing relative density and dielectric constant.

Comparing Examples 1, 3, and 4 or comparing Examples 2 with 5, a dielectric constant may vary depending on which metal element is disposed on the positions A and B of the second layer despite the same composition of the first layer.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A dielectric material, comprising
a layered metal oxide comprising a first layer having a positive charge and a second layer having a negative charge which are laminated, a monolayer nanosheet exfoliated from the layered metal oxide, a nanosheet laminate of the monolayer nanosheets, or a combination thereof,
wherein the dielectric material comprises a two-dimensional layered material having a two-dimensional crystal structure, and
the two-dimensional layered material is represented by Chemical Formula 1
Chemical Formula 1
$X_m[A_{(n-2)}B'_nO_{(3n+1)}]$ wherein in Chemical Formula 1, X comprises H, $Bi_2O_2$, a cationic compound, or a combination thereof,
A comprises Bi, Ba, Ca, Pb, Sr, or a combination thereof,
B' comprises W, Mo, Cr, Ta, Nb, Ti, or a combination thereof, and
$1 \leq m \leq 2$, and $n \geq 2$.

2. The dielectric material of claim 1, wherein the monolayer nanosheet comprises a second layer exfoliated from the layered metal oxide.

3. The dielectric material of claim 2, wherein the monolayer nanosheet comprises the cationic compound attached to a surface of the second layer.

4. The dielectric material of claim 1, wherein the two-dimensional layered material has an average longitudinal diameter of about 0.1 micrometers to about 100 micrometers.

5. The dielectric material of claim 1, wherein the two-dimensional layered material has an average thickness of less than or equal to about 100 nanometers.

6. The dielectric material of claim 1, wherein X comprises the cationic compound, and the cationic compound comprises a (C1 to C16 alkyl)ammonium compound, a (C1 to C16 alkyl)amine compound, or a combination thereof.

7. The dielectric material of claim 6, wherein the cationic compound comprises a tetramethylammonium compound, a tetraethylammonium compound, a tetrapropylammonium compound, a tetrabutylammonium compound, a methylamine compound, an ethylamine compound, a propylamine compound, a butylamine compound, an amine polymer, or a combination thereof.

8. The dielectric material of claim 1, wherein the dielectric material has a dielectric constant of greater than or equal to about 70 at a relative density of about 50% to about 90%.

9. A method of manufacturing the dielectric material of claim 1, comprising
preparing a layered metal oxide comprising a first layer having a positive charge and a second layer having a negative charge which are laminated,
acid-treating the layered metal oxide to exchange the first layer with protons,
colloidizing the acid-treated layered metal oxide to replace the protons by a cationic compound, and
exfoliating the monolayer nanosheet comprising the second layer from the colloidized layered metal oxide.

10. The method of claim 9, wherein the cationic compound comprises a tetramethylammonium compound, a tetraethylammonium compound, a tetrapropylammonium compound, a tetrabutylammonium compound, a methylamine compound, an ethylamine compound, a propylamine compound, a butylamine compound, an amine polymer, or a combination thereof.

11. The method of claim 9, wherein the monolayer nanosheet comprises the cationic compound attached to a surface of the second layer.

12. A dielectric device comprising
a plurality of crystal grains comprising a semi-conductive or conductive material, and
a grain boundary insulation layer between the crystal grains,
wherein the grain boundary insulation layer covers at least one portion of a surface of at least one of the crystal grains and a dielectric material comprising a two-dimensional layered material represented by Chemical Formula 1 and having a two-dimensional crystal structure:
Chemical Formula 1
$X_m[A_{(n-2)}B'_nO_{(3n+1)}]$ wherein, in Chemical Formula 1, X comprises H, $Bi_2O_2$, a cationic compound, or a combination thereof,
A comprises Bi, Ba, Ca, Pb, Sr, or a combination thereof,
B' comprises W, Mo, Cr, Ta, Nb, Ti, or a combination thereof,
$1 \leq m \leq 2$, and $n \geq 2$.

13. The dielectric device of claim 12, wherein the two-dimensional layered material comprises
a layered metal oxide comprising a first layer having a positive charge and a second layer having a negative charge which are laminated, a monolayer nanosheet exfoliated from the layered metal oxide, a nanosheet laminate of the monolayer nanosheets, or a combination thereof.

14. The dielectric device of claim 12, wherein the two-dimensional layered material covers an entire surface of at least one of the crystal grains.

15. The dielectric device of claim 12, wherein the cationic compound comprises a (C1 to C16 alkyl)ammonium compound, a (C1 to C16 alkyl)amine compound, or a combination thereof.

16. The dielectric device of claim 12, wherein the two-dimensional layered material is present in an amount of about 10 volume % to about 100 volume %,
based on 100 volume % of the grain boundary insulation layer.

17. The dielectric device of claim 12, wherein the crystal grains comprise barium titanate, strontium titanate, lead titanate, lead zirconate, lead zirconate titanate, or a combination thereof.

18. The dielectric device of claim 12, wherein the crystal grains have an average particle diameter of about 50 nanometers to about 1.5 micrometers.

19. An electronic device comprising the dielectric device of claim 12.

20. The electronic device of claim 19, wherein the electronic device is a varistor, a thermistor, or an energy storage capacitor.

\* \* \* \* \*